United States Patent [19]
Bond et al.

[11] Patent Number: 5,078,152
[45] Date of Patent: Jan. 7, 1992

[54] METHOD FOR DIAGNOSIS AND/OR TRAINING OF PROPRIOCEPTOR FEEDBACK CAPABILITIES IN A MUSCLE AND JOINT SYSTEM OF A HUMAN PATIENT

[75] Inventors: Malcolm L. Bond, Winters; Philip T. Dempster, Davis, both of Calif.

[73] Assignee: Loredan Biomedical, Inc., Davis, Calif.

[21] Appl. No.: 280,177

[22] Filed: Dec. 25, 1988

Related U.S. Application Data

[63] Continuation of Ser. No. 877,117, Jun. 23, 1985, abandoned.

[51] Int. Cl.$^5$ ............................................. A61B 5/103
[52] U.S. Cl. .................................. 128/774; 128/25 R; 272/DIG. 6
[58] Field of Search ................. 272/DIG. 5, DIG. 6, 272/129; 128/25 R, 774–781

[56] References Cited

U.S. PATENT DOCUMENTS

| | | | |
|---|---|---|---|
| 3,675,640 | 7/1972 | Gatts | 272/69 |
| 4,235,437 | 11/1980 | Ruis et al. | 901/9 |
| 4,244,021 | 1/1981 | Chiles | 272/73 |
| 4,354,676 | 10/1982 | Ariel | 272/129 |
| 4,934,694 | 6/1990 | McIntosh | 272/129 |

Primary Examiner—Francis Jaworski
Assistant Examiner—Scott R. Akers
Attorney, Agent, or Firm—Townsend and Townsend

[57] ABSTRACT

A method for diagnosis and/or training of proprioceptor feedback capabilities of a muscle and joint system of a human patient using an exercise system having a patient attachment device and an arrangement for controlling parameters of an exercise movement in response to a control signal derived from one or more measured exercise parameters. A patient performance goal is defined as a real time function of preselected exercise parameters. A perturbation signal function is defined for the control signal; and the control signal is modified by the perturbation function value during a patient exercise motion. The defined performance goal is displayed during the patient exercise motion and the actual patient performance relative to the performance goal is also tracked and displayed. An error value is measured as the difference between actual patient performance and the patient performance goal.

31 Claims, 5 Drawing Sheets

METHOD FOR DIAGNOSIS AND/OR TRAINING OF PROPRIOCEPTOR FEEDBACK CAPABILITIES IN A MUSCLE AND JOINT SYSTEM OF A HUMAN PATIENT

This application is a continuation of my copending U.S. application Ser. No. 06/877,117, now abandoned, filed June 23, 1985.

This invention relates generally to exercise systems and methods and, more specifically, to a method for diagnosis and training of proprioceptor feedback capabilities of a muscle and joint system of a human patient using an exercise system having a patient attachment device and an arrangement for controlling parameters of an exercise movement in response to a control signal.

Proprioception of human joints involves neural mechano-receptors associated with the joint, tendon and spindle receptors in the muscle associated with joint movement. These receptors have been categorized as either position sense receptors or dynamic sensing receptors, i.e. for sensing velocity of movement. A number of mechanisms have been proposed as being responsible for proprioceptive sensing. One theory is that the joint mechano-receptors project their output directly onto the muscle spindle system and set the gain or threshold of the spindle nerve fibers response to muscle stretch. The perception of stretch to the muscle when the muscle spindle system is at high gain shortens the time required for coordinated muscle contractile response and produces greater motor control in a particular movement. Any stress on the mechano-receptors in the joint capsule is relayed to the spindle system, which in turn adjusts the muscle tone to suit the situation.

Injury to a human extremity may be associated with direct damage to muscle tissue. Artificial immobilization during biological repair of muscle tissue may produce pathological disuse atrophy of the muscle tissue. Conventional rehabilitation of the extremity after injury and healing usually involves diagnosing and retraining the functionality of the involved joint with the status of rehabilitation inferred from parameters such as range of joint motion, attainment of normal muscular strength and normal fatigue resistance. However, even after rehabilitation with reference to these parameters, it is likely that subtle differences still remain in the peripheral neurosensory organs in the involved joint and related musculature. Deficiencies in the performance of these neurosensory organs affect the proprioceptive feedback system which is used to produce coordinated movement of the joint. The implications of such remaining damage after rehabilitation are important, particularly in normal human gait activities (e.g. walking and running) and specialized movements in sports activity where proprioception plays a fundamental role in the quantitative control, organization and timing of body action. It is believed that remaining damage in peripheral neurosensory organs may be responsible for cases of repetitive injury. In other words, although strength of the joint and muscle associated therewith may have been rehabilitated, remaining damage to the proprioceptive feedback mechanisms may preclude sufficiently coordinated movement to avoid reinjury during either normal human activity or specialized sports movements.

In the case of direct injury to the joint mechano receptors, as sometimes occurs in joint sprains, the patient is unable to exhibit coordinated movement about the joint during a weight bearing exercise event. The diagnosis of this condition appears to be that the muscle spindles are deficient in sensory input due to the damage to the mechano receptors in the articular structures associated with the joint.

Very little research has been done to evaluate proprioception integrity. One test that has been developed for evaluation of proprioception integrity is to analyze and grade the response of the muscles engaged in controlled movement to the sudden application of a resistance force. In one research project the application of resistance was provided by a breakaway trip wire attached to the foot of the patient. Electromyographic studies of the muscles provided evaluation capability for determining the muscular response The graded score of proprioception integrity was determined by the latency time between the application of resistance and the muscular response to return to a normal gait movement. The shorter the time, the tighter the neural control of position and velocity duplication ability of the involved joint and associated muscles.

It is the principal object of this invention to provide a method for diagnosis and/or training of proprioceptor feedback capabilities of a muscle and joint system of a human patient using a controllable exercise system which ran provide a variety of perturbation signals in one or more exercise control parameters associated with the system.

More specifically, it is an object of this invention to provide a method for diagnosis and/or training of proprioceptor feedback capabilities in a muscle and joint system using a controllable resistance exercise system.

It is another object of this invention to provide a methodological capability for assessing the effectiveness of controllable exercise systems in diagnosis of proprioceptive feedback integrity.

In its broadest aspects, this invention features a method for diagnosis and training of proprioceptor feedback capabilities of a muscle and joint system of a human patient using an exercise system having a patient attachment device together with means for controlling parameters of an exercise movement in response to a control signal derived from one or more measured exercise parameters. The steps of the method include defining a patient performance goal as a real time function of preselected exercise parameters. A perturbation signal function is defined for the control signal and preferably that perturbation signal function applies regular unexpected changes in the exercise system control signal so that the system can determine the adaptive response capability associated with the integrity of the proprioceptive neurosensory feedback loop in the body. The method also includes modifying the control signal by the perturbation function value during a patient exercise motion. To implement the biofeedback aspect, the defined performance goal is displayed during the patient exercise motion and the actual patient performance relative to that goal is also displayed during the patient exercise motion. An error value is measured as the difference between actual patient performance and the patient performance goal during the patient exercise motion.

The advantage of the method of this invention is that it permits quantification of the proprioception neurosensory feedback integrity. It is also expected that the invention will provide for retraining of these neurogenic components of muscle contraction as a separate aspect of a patient rehabilitation program. Since this is field of research and development which is in its infancy, the main initial value and advantage of this invention lies in its use as a research tool. The degree of effectiveness of diagnosis and training of proprioceptor feedback capabilities will await extensive research studies. However, the current foundation of knowledge regarding proprioceptor feedback and the method of this invention provide reasonable basis for concluding that at least some system implementations of the method of this invention have a strong probability of producing very significant diagnostic capabilities and proprioceptive feedback retraining capabilities.

Figure 1:
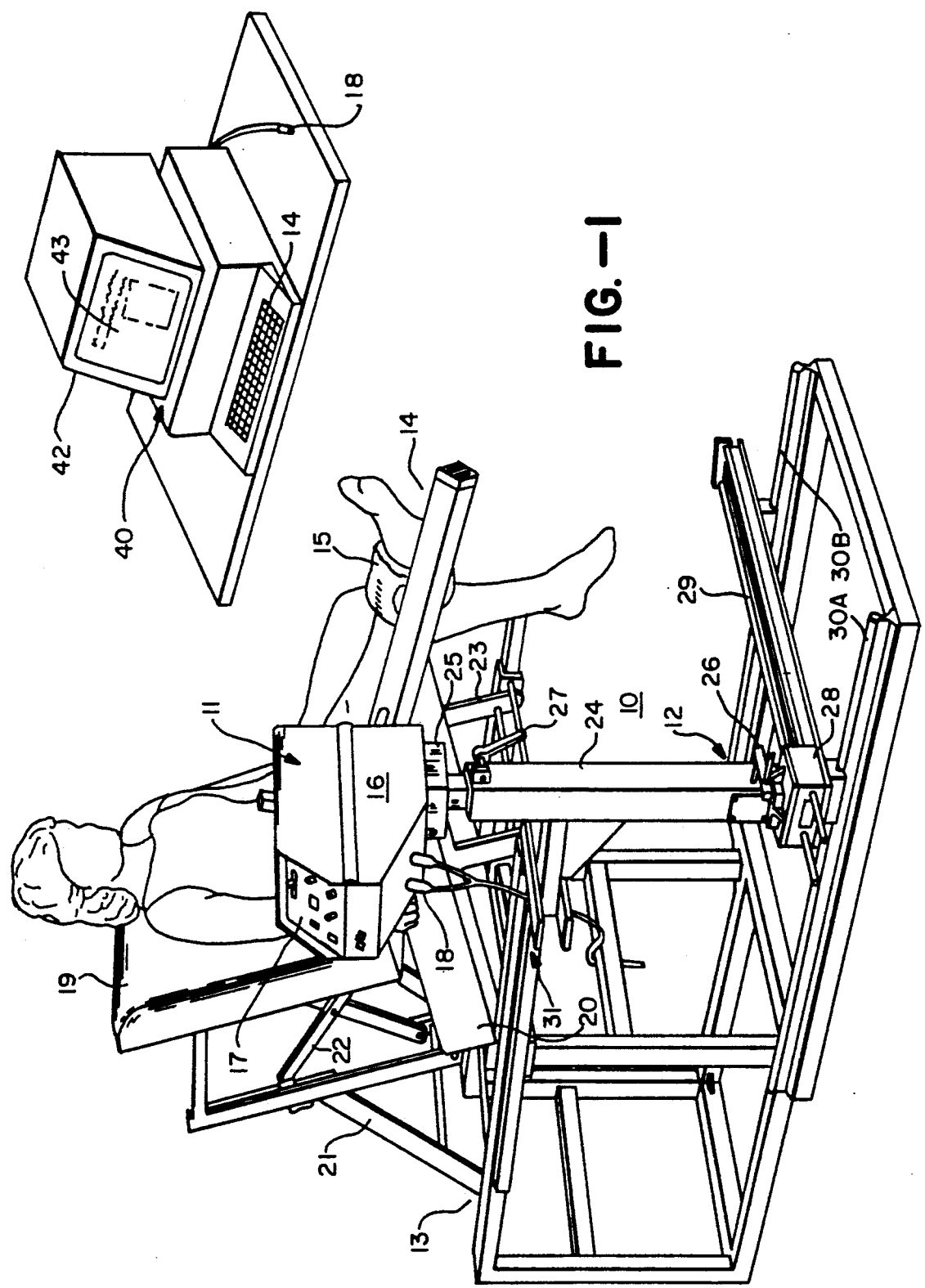
FIG. 1 is an isometric drawing of an isokinetic station comprising an exercise system which is capable of carrying out some versions of the method of this invention.

The method of this invention may be carried out in an isokinetic exercise system of the type shown in FIG. 1 as well as a variety of other exercise systems. The isokinetic station of FIG. 1 is a whole body system which has been designed for maximum utility in patient positioning, optimum flexibility in set up for exercise of various portions of the human body, and minimum involved floor space. This system is the one on which the method of this invention has been implemented at this time and this system is fully disclosed in the below-referenced copending and commonly assigned Bond et al. patent application which is incorporated herein by reference and hereafter referred to as the "Copending Bond Application."

Referring to FIG. 1, isokinetic station 10 includes a passive exercise resistance system 11, a mounting arrangement 12 and a patient couch 13. The passive resistance system 11 includes a lever arm assembly 14, a patient attachment cuff 15, a housing 16 which contains the passive resistance component of the system along with electronic controls. The housing 16 further includes a control panel 17 and output leads 18 which feed measurement signal outputs to a chart recorder and/or to a computer data acquisition unit 40. The details of this passive exercise resistance control system will be given below in connection with other drawing figures. The structural and functional details of various embodiments of lever arm assembly 14 and patient attachment cuff 15 are set forth in the Copending Bond Application. As disclosed therein, lever arm assembly 14 has patient attachment cuff mounted to the lever arm assembly in a manner such that the patient attachment point is free to move radially during an exercise motion.

The patient couch arrangement 13 includes two cushion portions 19 and 20 which, together with various positioning elements, provide for positioning of a patient in a sitting or reclining orientation, which is selected depending on the patient limb being exercised. In the set-up shown in FIG. 1, the cushion portion 19 is serving as a backrest and the cushion portion 20 is serving as a seat. A pair of positioning members 21 controls the angular orientation of the cushion portion 19 and a scissors jack type of positioning arrangement 22 controls the forward and backward position of the cushion portion 19.

Positioning supports 23 control the angle of the cushion element 20. To put the patient in a reclining position, the positioning members 23 and 21 are reoriented so that the cushion elements 19 and 20 are horizontal and in line with each other.

The mounting and positioning system 12 includes a vertical pedestal arrangement 24 which includes a rotary support member 25 to which the housing of the passive resistance system 16 is attached. Preferably a detent arrangement is provided such that the angular orientation of the lousing 16 relative to the patient couch can be selectively altered to fixed angles. A height adjustment jacking arrangement operated by the jack handle 26 is provided within the pedestal 24 to raise and lower the housing 16 for positioning of the axis of rotation of the lever arm assembly 14 relative to the patient.

The pedestal assembly 24 is mounted on a bearing slide arrangement 28 which permits side-to-side movement of the pedestal assembly 24 relative to the patient couch. Another bearing and track arrangement 30A and 30B permits front-to-back movement of the pedestal 24 carried on the bearing and track arrangement 28 and 29. A stabilizing arrangement 31 is provided to rigidly fix the pedestal 24 in a particular selected position relative to the patient couch assembly 13.

The remote computer system 40 includes a keyboard 41, and a display device 42 having a display screen 43. This remote computer system carries out the software routines associated with the method of this invention based on data that is acquired from the real time control computer in the exercise control unit 16 and on control signals that are sent back to the real time control computer. The display screen 43 displays to the patient exercising on the system the current value of the exercise parameter associated with a preselected exercise goal and the actual parameter value which is being attained by the patient. The details of this display will be discussed.

Figure 2:
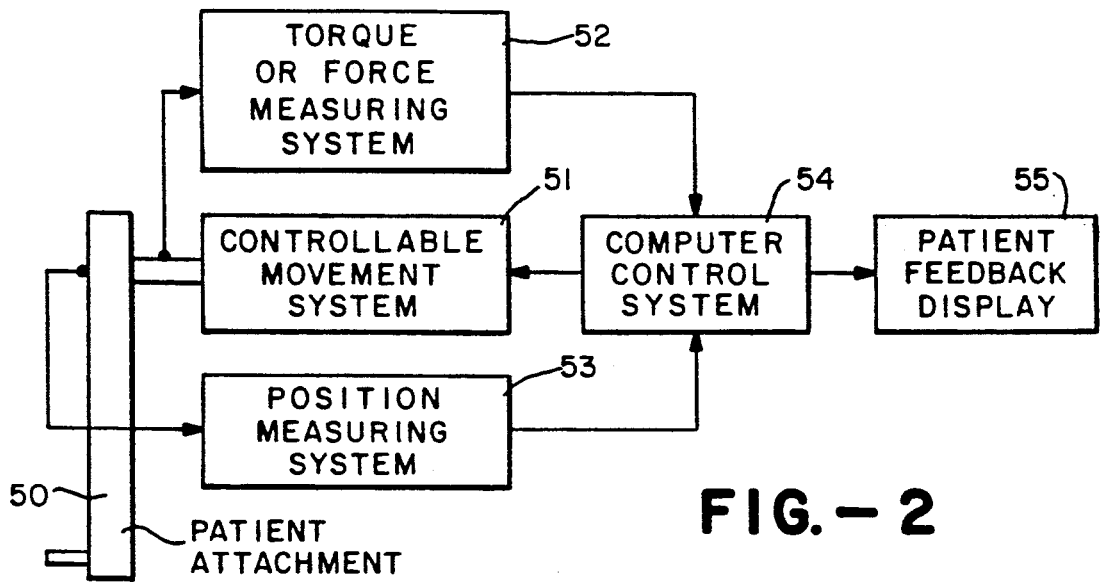
FIG. 2 is a general block diagram of exercise system components which are basic to the performance of the method of this invention.

FIG. 2 illustrates the basic components of an exercise system which are required for carrying out the method of this invention. The required system features include a patient attachment arrangement 50 and a controllable movement system 51 which may be one or both of an active or passive system. A torque or force measuring system 52 and a position measuring system 53 determine exercise parameters and feed signals to computer control system 54. Computer control system 54 runs a software program to provide an exercise control signal to the controllable movement system 51. Computer control system 54 also provides an output to a patient feedback display on which both the exercise goal and the actual value of exercise parameter may be displayed back to the patient.

Figure 3:
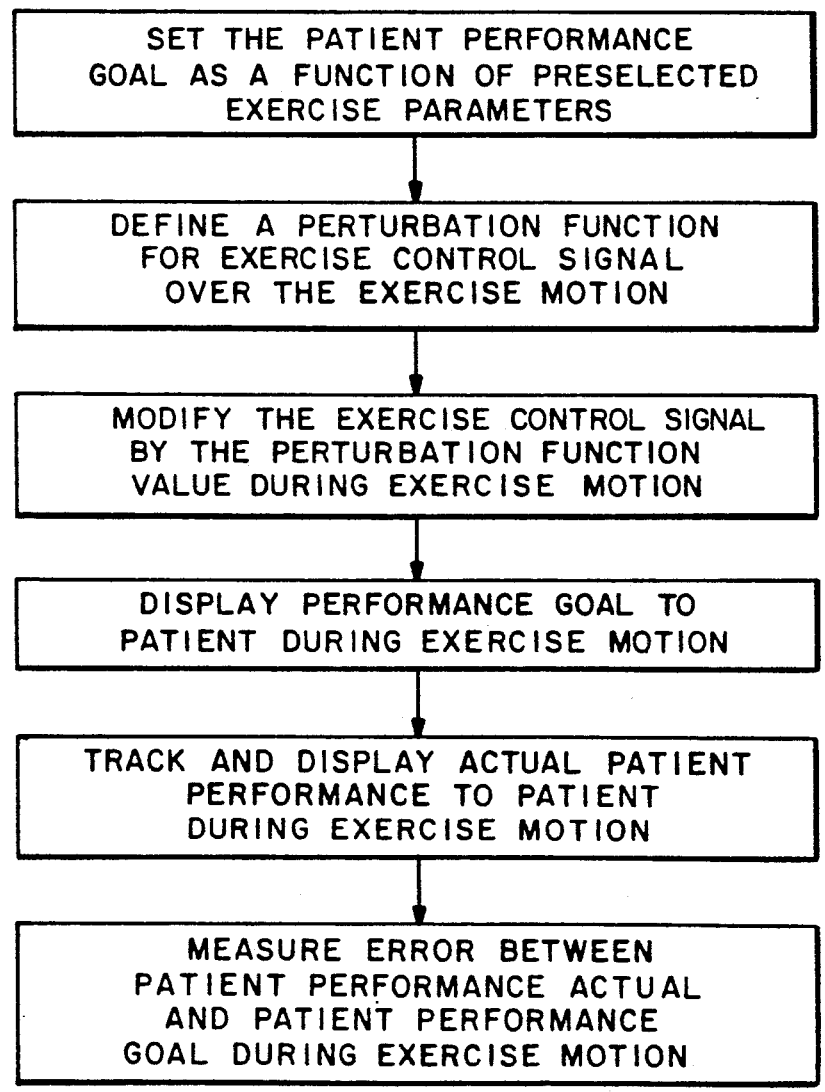
FIG. 3 is a generalized flow diagram setting forth the basic method steps of this invention.

FIG. 3 illustrates the basic steps of the method of this invention for diagnosis and training of proprioceptor feedback capabilities. The first step of the method involves defining a patient performance goal as a function of preselected exercise parameters. This patient performance goal may, for example, be related to position of the patient attachment system as a function of time, force or torque on the system as a function of position or some other parameter, or velocity as a function of some other parameter. Other possibilities for patient performance goals are such things as applied power as a function of position and the like.

A following step in the method is defining a perturbation function for the exercise control signal over the exercise motion. It is preferable that the perturbation function be one that alters the exercise control signal in at least a semi-random manner so that the perturbations experienced by the exercising patient are not predictable in time or both time and amplitude.

The method also involves modifying the exercise control signal by the perturbation function value during the exercise motion. This is preferably done on a proportional basis so that the exercise control signal does not move out of the range of the patient's ability to adapt to the perturbation based on the patient's strength.

Another step of the method involves displaying the defined patient performance goal to the patient during the exercise motion along with the step of tracking and displaying actual patient performance relative to the defined goal during the exercise motion. In this manner, the patient is able to utilize visual biofeedback to attempt to track the displayed performance goal despite the perturbations being introduced into the exercise control signal.

Another important step of the method involves measuring the error between the patient performance actual and patient performance goal during the exercise motion. Assuming serious and determined attempts by the patient to match performance of the exercise motion to the displayed performance goal, the error measurements should provide an indication of proprioceptor feedback integrity of the muscles and joint involved in the exercise motion. It should be appreciated that a wide variety of qualitative and quantitative error analysis methods can be experimented with to assess the ability of the method of this invention to quantitate the integrity of the proprioceptor feedback capabilities of the patient. The error analysis can include such simple analysis algorithms as cumulating error measurements over selected portions of the exercise motion. The error analysis may also include sophisticated Fourier analysis of the spectral content of the error signal which may eventually provide information on the type and degree of proprioceptor feedback deficiency.

Figures 4, 5:
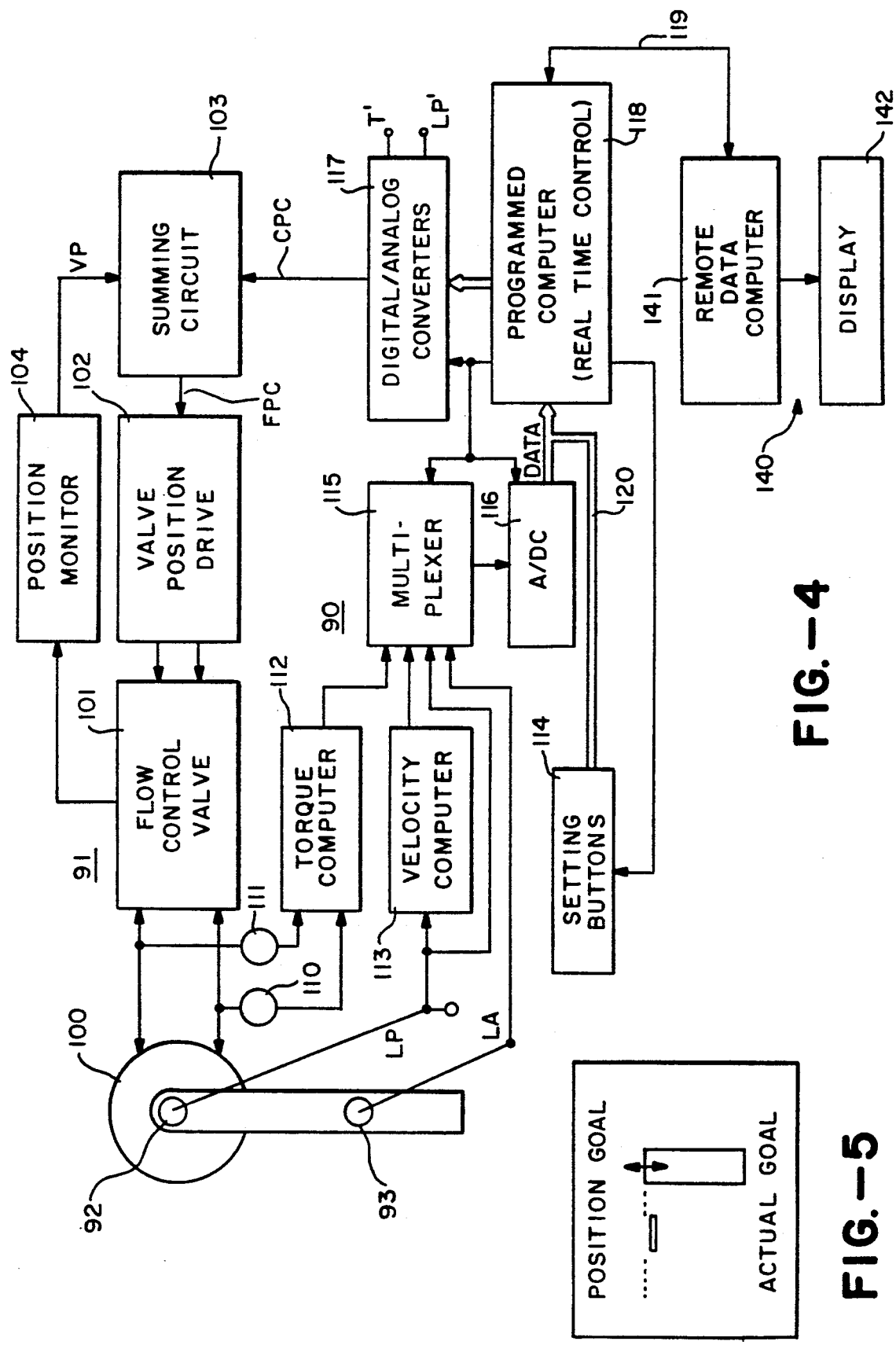
FIG. 4 is a block diagram of a particular form of digital real time control exercise system which may be used to perform specific embodiments of the method of this invention.
FIG. 5 is a pictorial display of a sample feedback display aspect of one embodiment of the method of this invention.

FIG. 4 is a block diagram which illustrates a digital signal processing version of a velocity control computer 90 useful in carrying out the method of invention. A torque computer 112 and a velocity computer 113 have their outputs coupled into multiplexer 115 along with the actual lever length signal LA and the lever position signal LP. The setting buttons 114 provide data on a dataline 120 under programmed computer control. Multiplexer 115 functions under the control of programmed computer 118 to multiplex one of the input analog signals to the analog to digital converter 116. Analog to digital converter 116 functions under computer control to convert the analog signal at its input to a digital data signal for input to the programmed computer 118. Digital to analog converters 117 receive output data from the programmed computer 118 and function under its control to provide output analog signals. One of these output analog signals is the compensated position control signal CPC. The other two output signals are torque T' and lever position LP' representing correct values for these parameters. As disclosed in the Copending Bond Application, rotational velocity governing system 91 includes a valve position drive 102 which controls the position of the flow control valve 101. A position monitor arrangement 104 is used to monitor the position of the flow control valve spool and the output position signal is fed back to an error circuit 103 to provide an inner servo loop which minimizes overshoot and other troublesome operational characteristics of the flow control valve.

Velocities control computer arrangement 90 includes a torque computer 112 which computes a torque value based on the relative output signals from pressure transducer 111 and 1 10 coupled into flow lines between flow control valve 101 and hydraulic actuator 100. This computation is basically an analog difference computation.

Functional computations are provided by the programmed computer 118 which processes the input analog signals to produce an appropriate compensated position control signal, first as a digital word value which is then output to a digital to analog converter 117 which converts it to an appropriate analog signal CPC for use by the summing circuit 103 to control the actual flow control valve position. The compensated position control signal CPC is calculated on the basis of certain velocity and torque correction factors which improve the accuracy of overall system control. A length measuring system 93 is operatively associated with a translating limb attachment arrangement (not shown) to continuously monitor the distance from the point of attachment of the human body to the axis of the shaft (not shown) of hydraulic acuator 100 during an exercise motion. This length measuring system may comprise a potentiometer operatively connected to the limb attachment to register the length as a proportional resistance. The output signal from the length measuring system 93 is coupled into velocity control computer 90.

As angle measuring system 92 is appropriately coupled to the shaft (not shown) of actuator 100 via some mechanical linkage to continuously monitor the angle of the lever arm. This function can be readily performed by a rotary potentiometer attached to the shaft. The output signal from the angle measuring system is also coupled into the velocity control computer 90.

The programmed computer 118 which provides real time control of the exercise system is coupled via a data link 119 to a remote data computer system 140. The remote data computer system 140 includes a programmable computer 141 that executes software routines involved in carrying out the method of this invention in this system embodiment. A display device 142 coupled to the computer 141 provides one form of the patient feedback display capability required for implementing the method of the invention.

It is seen from FIG. 4 that there are two analog computer circuit systems remaining in the velocity control computer system in this particular implementation. The torque computer 112 and the velocity computer 113 are conveniently implemented in analog computer circuitry to reduce the number of digital inputs that have to be taken into the programmed computer. It should be understood that the torque computation could be accomplished by separately multiplexing and converting the outputs of the pressure transducer subsystems 110 and 111. It should also be understood that the velocity computation could be made by the programmed computer instead of utilizing an analog version of that computational function.

The details of a specific embodiment of real time control software being executed in the programmed computer 118 is given in a co-pending and commonly assigned Bond et al. patent application Ser. No. 845,861, filed Mar. 28, 1986. The disclosure of this co-pending application is hereby incorporated by specific reference to complete the specific details of a working system embodiment for carrying out the method of this invention. The passive, isokinetic exercise system depicted in FIG. 4 is not the only type of system in which the method of this invention could be carried out. Generally, this invention should be adaptable to any exercise system, active or passive, in which electronic control over the basic system parameters affecting the movement of the system by the patient is provided.

FIG. 5 illustrates a type of patient feedback display that may be used in connection with this invention. A position versus time goal is displayed with the goal bar moving up and down to indicate the goal of the lever position relative to time after turnaround from the maximum extension and flexion of the exercise movement. The display of the actual position shows the patient the actual lever position relative to the goal so that the patient can try to track the goal position as accurately as possible. In the algorithm implemented in one version of this invention, the goal display displays position as a function of time but only begins to change in a positive or negative direction after the patient reaches the actual limit of exercise motion and turns around with sufficient application of torque on the lever arm to signal a turnaround. It should be apparent that other algorithms for displaying the patient position goal could be implemented.

Figure 6:
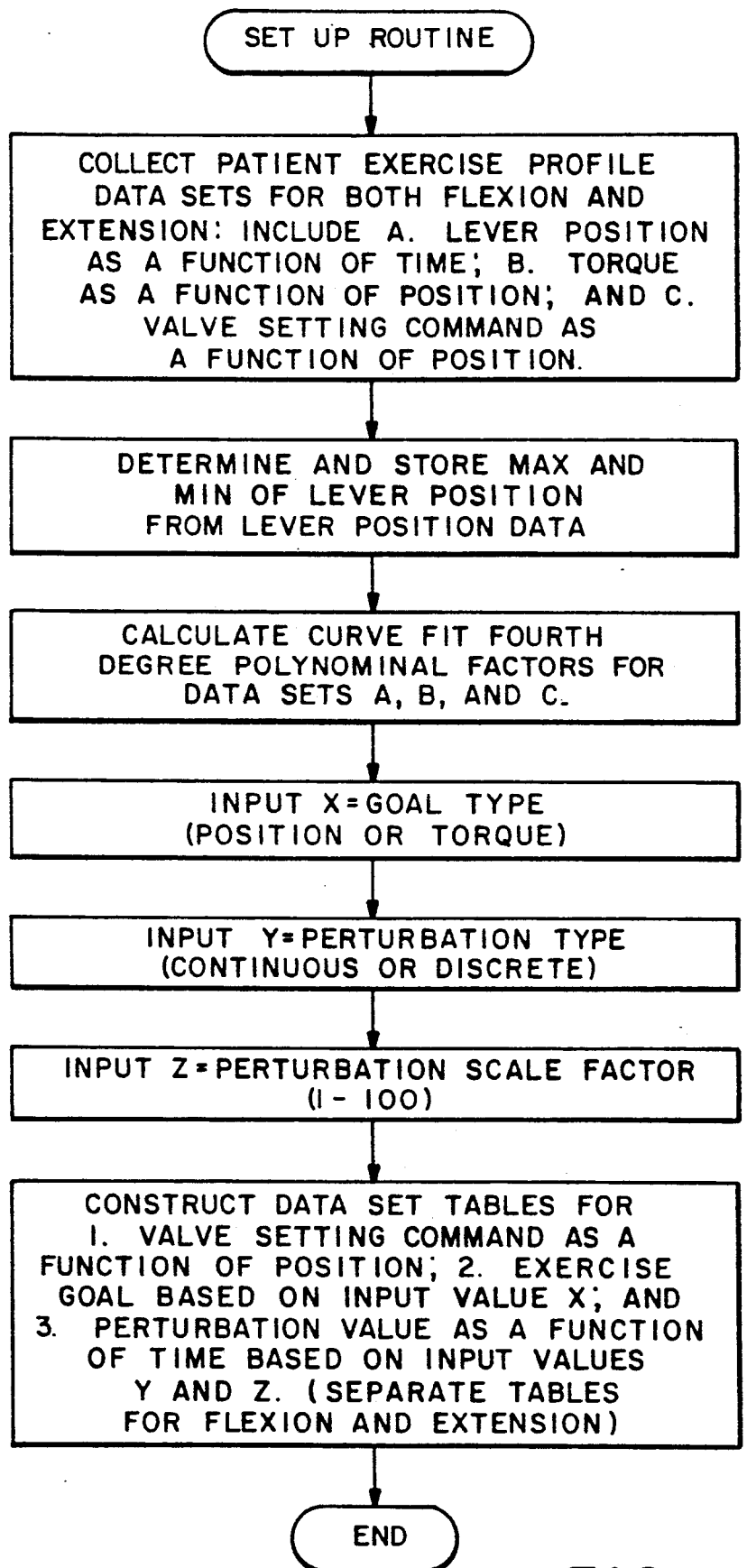
FIGS. 6 and 7 illustrate generalized software routines which may be implemented in the system of FIG. 4 to perform specific embodiments of the general method of this invention.
Figure 7:
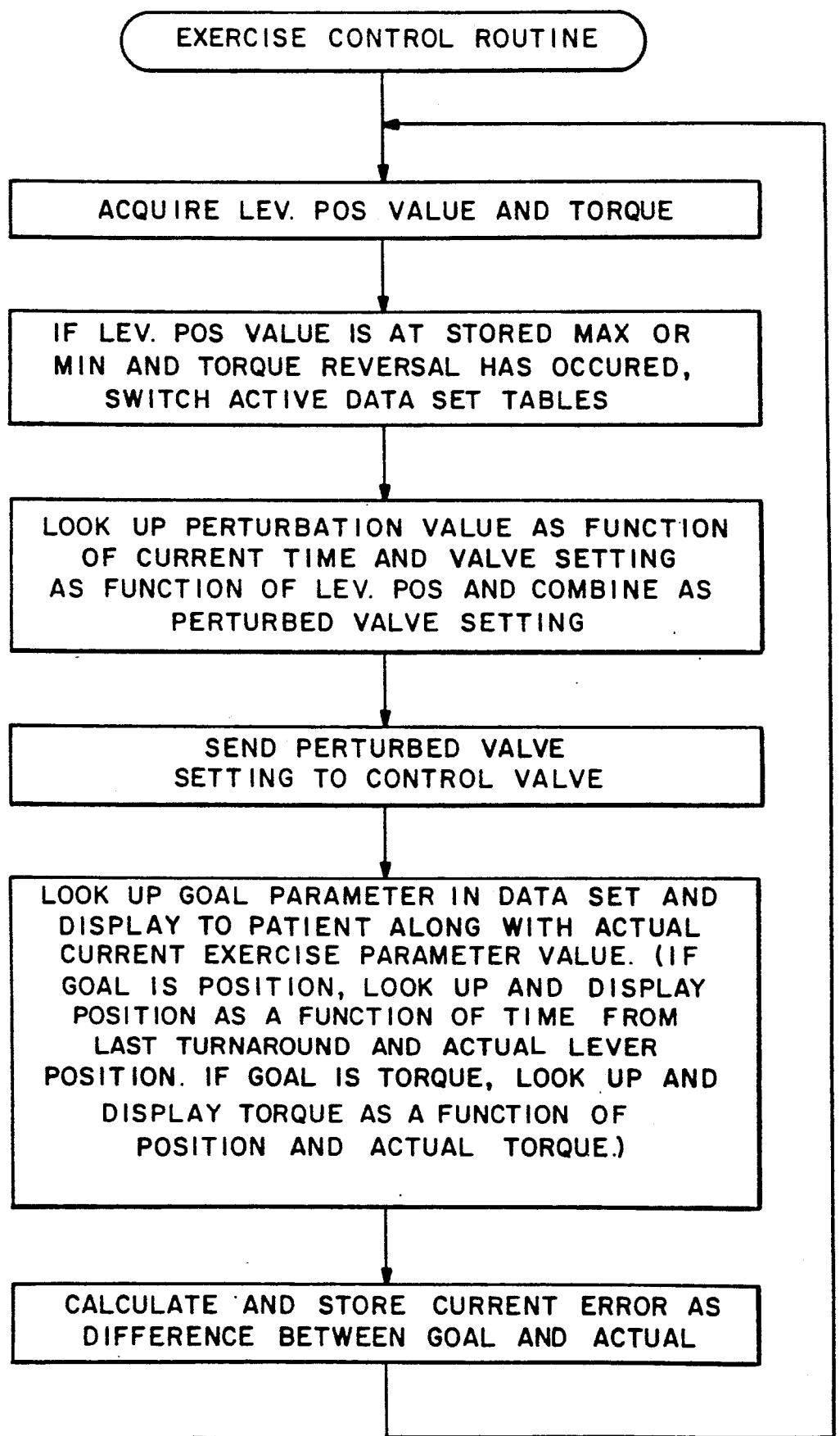

FIGS. 6 and 7 illustrate the general steps of a set-up routine and an exercise control routine in accordance with one embodiment of the method of this invention as implemented on the system of FIG. 4. These routines are carried out in the remote data computer 141 in the case of the system of FIG. 4. It should be understood however that, in other systems configurations it may be possible to combine the functions of the real time control computer 118 and the remote data computer 141 into a single computer control and data analysis system.

The set-up routine depicted in FIG. 6 implements a version of the method of this invention in which the patient performance goal is defined on a basis of patient exercise profile data which is collected during several repetitions of the exercise motion on the system. Accordingly, the first general step of this set-up routine involves collecting patient exercise profile data sets for both the flexion and extension movements. These data sets include a data set A comprising lever position as a function of time, a data set B involving torque as a function of position and a data set involving valve setting command as a function of position. A subsequent step of the method involves determining and storing the maximum and minimum lever positions of the patient's exercise motion from the lever position data which has been stored. It should also be understood that the MAX and MIN lever position information could be obtained from the upper and lower limit settings which may be set in using the setting buttons 114 shown in FIG. 4. Reference is made to the co-pending patent application referred to above for an explanation of these limits setting functions.

Another step of the method then involves calculating curve fit fourth degree polynomial factors for the data sets A, B and C referred to above. In this manner a smooth curve is fit to the acquired data so that, there necessary in later control functions, appropriate data parameters can be obtained over the whole range of data values. These curve fit polynomial factors are stored for later use.

The next steps of the method involve inputting certain set-up selections such as goal type, perturbation type and perturbation scale factor. In the current implementation of the invention the goal types are selectable to be either a position goal or a torque goal. The position goal involves lever or shaft position as a function of time. The torque goal involves torque value as a function of lever or shaft position. The perturbation types available in the current implementation involve either a continuous type of perturbation or a discrete perturbation. In the continuous type of perturbation the transition between perturbation values applied to the valve setting command signal (discussed later) provide a relatively smooth change in the amplitude of the perturbation signal. In the discrete case, the perturbation amplitude varies between two values with the time of the change between values being substantially random. The perturbation scale factor is currently set from 1 to 100. This input determines the amplitude of the perturbation applied to the valve setting command.

After these inputs have been received, the routine constructs data set tables for the valve setting command as a function of position, the exercise goal based on input x for goal type and the perturbation value as a function of time based on the input values y and z. Separate data set tables are constructed for flexion and extension since the patient profile data varies for those exercise motions.

The real time control software described in the above-mentioned co-pending patent application utilizes logarithm values for the valve setting command. Accordingly, it is preferred that the valve setting command table and the perturbation value table be structured as logarithm tables so that these values can be added together to achieve automatic proportioning of the perturbation to the degree of resistance which is commanded by the valve setting command.

After these data set tables have been constructed, the patient can begin to exercise on the system while the remote data computer 141 shown in FIG. 4 is running the exercise control routine. It should be understood that during this proprioception feedback exercise approach, the valve setting command which is normally sent to the circuitry which operates the flow control valve is interrupted so that a perturbed valve setting can be sent to the flow control valve under the control of the remote data computer. The valve setting command determined by the programmed computer 118 would provide isokinetic control over the movement of the lever arm which is not desired under this proprioceptive exercise approach.

The exercise control routine shown in FIG. 7 includes acquiring the lever position value and torque value determined by the programmed computer 118. The routine determines whether the lever position value is at the stored maximum or minimum and whether a torque reversal has occurred and switches the active data sat tables if these joint conditions are satisfied. This provides the system capability to utilize different data set table values during flexion and extension motions of the lever arm of the exercise system. The routine next looks up a perturbation value as a function of the current elapsed time and a valve setting as a function of the lever position and combines these values (summing them as logarithm values) to obtain a perturbed valve setting. It is this perturbed valve control setting which is then sent from the remote data computer 141 back to the real time control computer 118 to be sent to the flow control valve position control circuitry instead of the valve command setting calculated by the real time control computer 118.

The exercise control routine of FIG. 7 also looks up the goal parameter in the appropriate data set and displays this to the patient along with the actual current exercise parameter value. In this manner the patient can determine how close his performance is to the displayed goal and attempt to alter the exercise motion to track the displayed goal. If the goal type selection made in the set-up routine is a position goal the system looks up and displays the position as a function of time from the last turnaround as well as the actual lever position. If the goal is a torque goal, the routine looks up and displays torque as a function of position as well as the actual torque.

Another step of the method is to calculate and store current error as a difference between the goal and actual, i.e. the difference between the values of these parameters.

In addition to running the exercise control routine shown in FIG. 7, a number of other parameters are acquired by the remote data computer during the exercise routine so that that data can be stored, manipulated, and/or displayed utilizing appropriate program routines.

It should be understood that the set-up and exercise control routines depicted in FIGS. 6 and 7 provide a specific implementation of the general concepts of the method of this invention which could readily be altered in many different ways to achieve different specific functionality but remaining within the general concepts of this invention. It should be apparent that once the data has been accumulated for the error values between the exercise goal and actual patient performance, a wide variety of data display and printout routines could be implemented to visually display significant aspects of the data, and perform meaningful data analysis tasks.

While the method of this invention has been described above in the form of a general concept and certain specific embodiments, it should be understood that persons of school in the related art of this invention could make numerous modifications and additions without departing from the scope of the invention.

What is claimed is:

1. An apparatus for testing proprioceptor feedback mechanisms in a muscle and joint system of a patient comprising:
    goal defining means for defining a patient performance goal over a range of motion as a function of a selected exercise parameter;
    perturbation function means for defining a perturbation function over a portion of the range of motion;
    resistance applying means, coupled to the goal defining means, for applying resistance to movement of a part of the body of the patient in accordance with the patient performance goal;
    movement perturbing means, coupled to the perturbation function means and to the resistance applying means, for causing the resistance applying means to unexpectedly vary the resistance sufficiently to at least momentarily cause the movement of the patient's body part to deviate from the performance goal within the range of motion.

2. The apparatus according to claim 1 wherein the patient performance goal is an isokinetic performance goal, and wherein the movement perturbing means causes the resistance applying means to at least momentarily cause the part of the body to move nonisokinetically.

3. The apparatus according to claim 1 wherein the perturbation function is a function of time.

4. The apparatus according to claim 1 wherein the resistance applying means includes a shaft which rotates in response to movement of the patient's body part.

5. The apparatus according to claim 4 wherein the exercise parameter is a shaft position as a function of time.

6. The apparatus according to claim 4 wherein the exercise parameter is torque applied to the shaft as a function of shaft position.

7. The apparatus according to claim 4 wherein the exercise parameter is shaft velocity.

8. The apparatus according to claim 1 wherein the resistance applying means includes control means for producing a resistance control signal which determines the resistance applied to the movement of the patient's body part, the resistance control signal being derived from the function of the selected exercise parameter.

9. The apparatus according to claim 8 wherein the movement perturbing means modifies the resistance control signal with a value of the perturbation function during movement of the patient's body part.

10. The apparatus according to claim 9 wherein the perturbation function is a variable function defined over the entire range of motion.

11. The apparatus according to claim 9 wherein the movement perturbing means modifies the resistance control signal in a semi-random manner.

12. The apparatus according to claim 9 wherein the movement perturbing means modifies the resistance control signal for producing a sudden change in the resistance applied to the movement of the patient's body part.

13. The apparatus according to claim 9 wherein the movement perturbing means modifies the resistance control signal for producing a sudden and unexpected change in the resistance applied to the movement of the patient's body part.

14. A method for testing proprioceptor feedback mechanisms in a muscle and joint system of a patient using a controllable resistance exercise system which applies resistance to movement of a part of the patient's body in response to a resistance control signal comprising the steps of:
    defining a patient performance goal over a range of motion as a function of a selected exercise parameter;
    defining a perturbation function over a portion of the range of motion;
    deriving the resistance control signal from the function of the selected exercise parameter;
    applying resistance to movement of a part of the body of the patient in accordance with the patient performance goal; and
    modifying the resistance control signal sufficiently to at least momentarily cause the movement of the patient's body part to deviate unexpectedly from the performance goal within the range of motion.

15. The method according to claim 14 wherein the patient performance goal is an isokinetic performance goal, and wherein the resistance control signal modifying step comprises the step of at least momentarily causing the part of the body to move nonisokinetically.

16. The method according to claim 14 wherein the perturbation function is a function of time.

17. The method according to claim 14 wherein the resistance applying step comprises the step of rotating a shaft in response to movement of the patient's body part.

18. The method according to claim 17 wherein the exercise parameter is a shaft position as a function of time.

19. The method according to claim 17 wherein the exercise parameter is torque applied to the shaft as a function of shaft position.

20. The method according to claim 17 wherein the exercise parameter is shaft velocity.

21. The method according to claim 14 wherein the resistance control signal modifying step further comprises the step of modifying the resistance control signal with a value of the perturbation function during movement of the patient's body part within the range of motion.

22. The method according to claim 21 wherein the perturbation function is a variable function defined over the entire range of motion.

23. The method according to claim 21 wherein the step of modifying the resistance control signal further comprises the step of modifying the resistance control signal in a semi-random manner.

24. The method according to claim 21 wherein the step of modifying the resistance control signal further comprises the step of modifying the resistance control signal for producing a sudden change in the resistance applied to the movement of the patient's body part.

25. The method according to claim 21 wherein the step of modifying the resistance control signal function comprises the step of modifying the resistance control signal for producing a sudden and unexpected change in the resistance applied to the movement of the patient's body part.

26. The method according to claim 14 further comprising the step of attempting, by the patient, to match the patient performance goal despite the deviation from the performance goal.

27. In a method for measuring proprioceptor feedback capabilities in a muscle and joint system of a human patient using a controllable resistance exercise system having a resistance value determined by a resistance control signal, the steps of:
defining a patient performance goal as a real time function of preselected exercise parameters;
defining a perturbation function for controllable resistance over an exercise motion;
modifying the resistance control signal by the perturbation function value during the exercise motion for unexpectedly altering the resistance value;
attempting, by the patient, to match the patient performance goal despite the alteration of the resistance value;
displaying said defined performance goal during the patient exercise motion;
tracking and displaying actual patient performance relative to said performance goal during the patient exercise motion; and
measuring as an error value the difference between actual patient performance and said patient performance goal during the exercise motion.

28. The method of claim 27, wherein said step of defining a patient performance goal comprises collecting data on one or more preselected exercise parameters during an actual exercise motion by the patient and defining said patient performance goal as a function of said collected data.

29. In a method for measuring proprioceptor feedback capabilities in a muscle and joint system of a human patient using a controllable resistance exercise system having a patient attachment device mounted for movement through space, a resistive component coupled to said patient attachment device to resist the movement of said patient attachment device with a resistance value determined by a resistance control signal, and having means for tracking position of said attachment, and means for tracking force applied to said attachment, the steps of:
profiling the parameters of actual patient exercise movements by collecting data on position of said attachment device as a function of time, force on said attachment device as a function of position, and the value of said resistance control signal as a function of position;
producing patient exercise profile curves from said collected data and storing representations of said profile curves;
deriving from said stored curve representations a patient goal performance function selected as one of position as a function of time and torque as a function of position;
defining a perturbation function for said stored curve representation for said resistance control signal value as a function of time;
applying during a subsequent patient exercise motion a resistance control signal value as a function of actual position derived from said patient exercise profile curves modified by the current value of said perturbation function for unexpectedly altering the resistance value;
attempting, by the patient, to match the goal despite the altered resistance value;
displaying said defined performance goal during said subsequent patient exercise motion;
tracking and displaying actual patient performance relative to said performance goal during said subsequent patient exercise motion; and
measuring as an error value the difference between actual patient performance and said patient performance goal during the subsequent exercise motion.

30. In a method for measuring proprioceptor feedback capabilities of a muscle and joint system of a human patient using an exercise system having a patient attachment device and means for controlling parameters of an exercise movement in response to a control signal derived from one or more measured exercise parameters, the steps of:
defining a patient performance goal as a real time function of preselected exercise parameters;
defining a perturbation signal function for said control signal;

modifying said control signal by said perturbation function value to produce an unexpected perturbation signal during a patient exercise motion;

attempting, by the patient, to match the performance goal despite said modified control signal;

displaying said defined performance goal during said patient exercise motion;

tracking and displaying actual patient performance relative to said performance goal during said patient exercise motion; and measuring as an error value the difference between actual patient performance and said patient performance goal during said patient exercise motion.

31. In a method for measuring proprioceptor feedback capabilities of a muscle and joint system of a human patient using a controllable resistance exercise system having a hydraulic actuator with complementary hydraulic fluid chambers and a shaft, a lever arm coupled to said actuator shaft and a flow control valve coupled to said actuator for controlling the degree of resistance applied to said lever arm by said actuator in response to a valve position command signal, means for measuring the lever position and means for measuring the torque applied to said shift, the steps of:

collecting and storing patient exercise profile data during a series of actual patient exercises on the system for both flexion and extension exercise movements, including collecting and storing data sets comprising lever position as a function of time from the last turnaround of the lever, torque as a function of lever position, and valve position command signal as a function of lever position;

determining from said stored lever position data a maximum and minimum lever position for said profiled patient exercise;

calculating curve fit polynomial factors for said stored data sets;

receiving and storing input goal type, perturbation type, and perturbation scale factor selections;

constructing and storing for each of flexion and extension exercise movements a set of data tables comprising valve setting command values as a function of lever position, exercise goal values based on input goal type, and perturbation values based on input perturbation type and scale factor;

receiving and storing values of current lever position and torque;

determining an active data set from current lever position and torque values;

selecting a perturbation value from said data table of perturbation values based on a time factor;

selecting an unperturbed valve setting command from said data table based on current lever position;

determining a perturbed valve setting command by combining said unperturbed valve setting command with said perturbation value;

communicating said perturbed valve setting command to said flow control valve to set the current value of exercise resistance to an unexpected perturbation value of said exercise resistance;

determining the current goal parameter value in said goal data set;

displaying said current goal parameter value and the associated current exercise value; and determining and storing a current error value based on the difference between said current goal parameter value and said associated current exercise value.

* * * * *